US00PP09362P

United States Patent [19]

Evison

[11] Patent Number: Plant 9,362

[45] Date of Patent: Nov. 7, 1995

[54] CLEMATIS NAMED EVITHREE

[75] Inventor: Raymond J. Evison, St. Sampson Guernsey, Great Britain

[73] Assignee: The Guernsey Clematis Nursery Limited, United Kingdom

[21] Appl. No.: 331,040

[22] Filed: Oct. 28, 1994

[51] Int. Cl.[6] ..... A01H 5/00

[52] U.S. Cl. ..... Plt./54.1

[58] Field of Search ..... Plt./54.1

*Primary Examiner*—James R. Feyrer
*Attorney, Agent, or Firm*—Christie, Pairr & Hale

[57] ABSTRACT

A new variety of clematis suitable for producing violet flowers having a dark contrasting central bar in the tepals and an attractive domed boss of stamens.

1 Drawing Sheet

BACKGROUND OF THE INVENTION

This invention relates to a new and distinct variety of Clematis. The varietal denomination of the new variety is 'Evithree'. It was discovered as a seedling in a controlled planting of cultivated plants in my nursery in St. Sampsons Parish, Guernsey, Channel Islands, Great Britain, and its parents are not known.

SUMMARY OF THE INVENTION

Among the features which distinguish the new variety from other presently available and known commercial clematis cultivars are the following combinations of characteristics: attractive violet flowers having a dark contrasting bar in the tepals and an attractive domed boss of stamens. 'Evithree' is asexually propagated by vegetative cuttings and asexual reproduction of new variety as performed by vegetative cuttings in Guernsey, Channel Islands, Great Britain, shows that the foregoing and other distinguishing charateristics come true to form and are established and transmitted through succeeding propagations.

BRIED DESCRIPTION OF THE ILLUSTRATION

The accompanying photographic illustration shows the foliage and flowers of the new variety with different flowers shown in various stages of maturity. The flower poise, contrasting colors, petal count and petal characteristics are depicted. The domed boss of stamens is shown forming the attractive center of the flowers and the color and character of the foliage can be seen behind the flowers. The coloration shown in the photograph is as nearly corrected as is possible in color illustrations of this character. Throughout the specification color values are based upon the *Royal Horticultural Colour Chart,* Royal Horticultural Society of London, England, except where common terms of color definition are employed.

DESCRIPTION OF THE NEW VARIETY

The following description is of clematis plants of the new cultivar grown under glass at Guernsey, Channel Islands, Great Britain throughout the flower period. Phenotypic expression may vary with environmental, cultural and climatic conditions, as well as differences in conditions of light and soil.

Classification: Clematis.

PLANT

A. Form: Upright, climbing or spreading.
B. Growth: Medium growth.

*Height attained.*—About 2.5 meters.

C. Foliage: Deciduous, compound — tri-folate, sometimes simple.
   1. *Size.*—Medium.
   2. *Quantity.*—Average.
   3. *Color.*—New foliage: Upper side — near 137D. Underside — near 137. Old foliage: Upper side — near 137B. Underside — near 137C.
   4. *Shape.*—Lower leaves sometimes simple; normally 3 elliptical leaflets in pinnate form.
   5. *Texture.*—Upper side — glabrous. Underside — ribbed and hairy.
   6. *Edge.*—Normal.
   7. *Serration.*—None.
   8. *Petiole color.*—Top surface — green. Underside — green.
   9. *Stipules.*—None.
   10. *Internodes.*—Describe: Cylindrical. Length: About 12 cm to about 17 cm.
   11. *Resistance to disease.*—Subject to any disease that normally affects clematis but less prone to mildew than some clematis.

D. Wood:
   1. *New shoots.*—Color — light green. Bark — smooth — light white hairs.
   2. *Old wood.*—Color — light brown. Bark — rough.

E. Hardiness: Zone 4–9.

FLOWER

A. Blooming habit: Recurrent.
B. Bud:
   1. *Size.*—About 4 cm to about 5 cm.
   2. *Form.*—Elliptic to ovate.
   3. *Color.*—Green/grey.

C. Sepals: None — tepals only.
D. Peduncle:
   1. *Length.13* About 10 cm to about 14 cm.
   2. *Aspect.*—Vertical.
   3. *Strength.*—Erect.
   4. *Color.*—Green, near 143C.

E. Bloom:
   1. *Size.*—About 14 cm to about 18 cm.
   2. *Borne.*—Singly.
   3. *Form.*—Tepals opening to become flat.
   4. *Petalage.*—6.
   5. *Color.*—Outer tepals: Top surface — violet, near 88A with red-purple central bar, near 77A. Undersurface — violet-blue, near 90C. Base of tepals: Violet, near 88A. General tonality from a distance: Violet with red strip.

6. *Color change.*—As bloom ages, all colors lighten. General tonality at a distance: Pale violet-blue.

F. Tepals:

1. *Texture.*—Medium.
2. *Appearance.*—Top surface — satiny. Under surface — matt.
3. *Form.*—Obovate.
4. *Arrangement.*—Regularly arranged.
5. *Petaloids in center.*—None.
6. *Persistence.*—Tepals persist.
7. *Fragrance, if any.*—None.
8. *Lasting quality on plant and after cutting.*—About two weeks on plants, lasting only a few days as a cut flower.

REPRODUCTIVE ORGANS

A. Stamens, filaments and anthers:

1. *Arrangement.*—Regularly arranged.
2. *Color.*—Stamens: White base, reddish brown tip. Filaments: Light violet base, becoming white. Anthers: Reddish brown.

B. Pollen:

*Color.*—Light brown.

C. Styles: Bunched, even, average length.

D. Stigmas:

*Color.*—White.

E. Hips:

*Shape.*—None.

I claim:

1. A new and distinct variety of clematis substantially as described and illustrated herein.

* * * * *

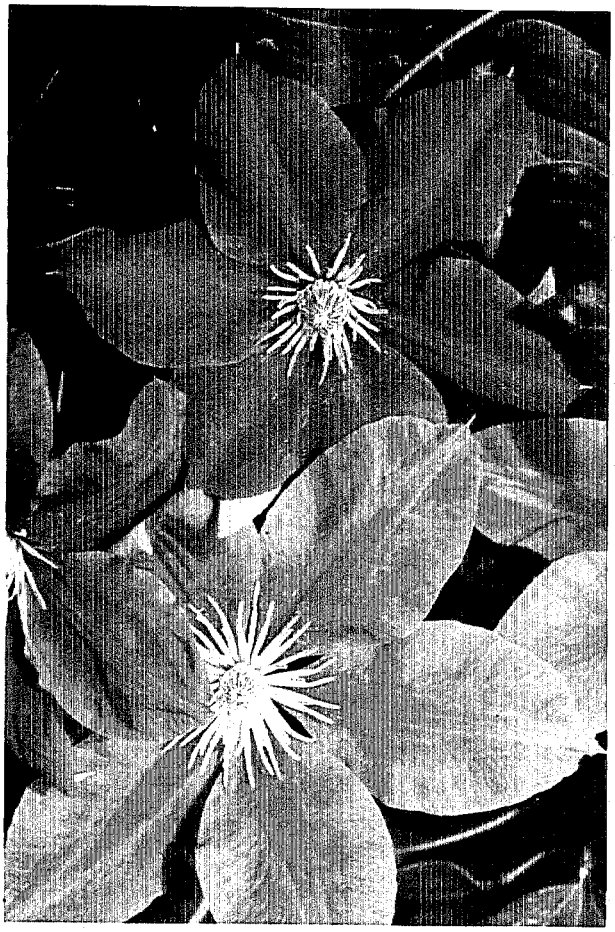

UNITED STATES PATENT AND TRADEMARK OFFICE

CERTIFICATE OF CORRECTION

PATENT NO. : Plant 9,362

DATED : November 7, 1995

INVENTOR(S) : Raymond J. Evison

It is certified that error appears in the above-indentified patent and that said Letters Patent is hereby corrected as shown below:

Column 1, lines 19, 20, change "charateristics" to -- characteristics --.

Column 1, line 22, change "BRIED" to -- BRIEF --.

Column 1, line 31, change "corrected" to -- correct --.

Column 2, line 37, after "*Length.*" delete "13".

Signed and Sealed this

Fourteenth Day of May, 1996

*Attest:*

Bruce Lehman

BRUCE LEHMAN

*Attesting Officer*

*Commissioner of Patents and Trademarks*